US006448276B1

(12) United States Patent
Yerxa

(10) Patent No.: US 6,448,276 B1
(45) Date of Patent: Sep. 10, 2002

(54) METHOD FOR TREATING VAGINAL DRYNESS WITH NICOTINIC ACETYLCHOLINE RECEPTOR AGONISTS

(75) Inventor: Benjamin R. Yerxa, Raleigh, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/574,831

(22) Filed: May 17, 2000

(51) Int. Cl.$^7$ ............................................. A61K 31/44

(52) U.S. Cl. ....................................................... 514/357

(58) Field of Search ........................................ 514/357

(56) References Cited

U.S. PATENT DOCUMENTS

| | | | | |
|---|---|---|---|---|
| 5,723,477 A | 3/1998 | McDonald et al. | ......... | 514/340 |
| 5,741,802 A | 4/1998 | Kem et al. | ................... | 514/334 |
| 5,817,679 A | 10/1998 | Shen et al. | ................ | 514/339 |
| 5,830,904 A | 11/1998 | Crooks et al. | .............. | 514/317 |
| 5,861,423 A | 1/1999 | Caldwell et al. | ............ | 514/351 |
| 5,922,723 A | 7/1999 | Bencherif et al. | .......... | 514/256 |
| 6,248,744 B1 * | 6/2001 | Eisenach | .................... | 514/256 |

FOREIGN PATENT DOCUMENTS

WO    WO 97/46554    11/1997

OTHER PUBLICATIONS

Arheric, Stephen P. and Jorge D. Brioni., Neuronal Nicotinic Receptors: Pharmacology and Therapeutic Opportunities, Eds. Arneric and Brioni, Wiley–Liss, Inc. (1999) (table of contents only).
Badio, Barbara., et al., "Synthesis and nicotininc activity of epiboxidine: an isoxazole analogue of epibatidine," *Eur. J. Pharmacol.* 321:189–194 (1997).
Benowitz, Neal L., et al., "Pharmacokinetics and Metabolism of Nicotine and Related Alkaloids," *Neuronal Nicotinic Receptors*, Eds. Arneric and Brioni, Wiley–Liss, Inc. 213–234 (1999).
Brioni, Jorge., et al., "Nicotinic Receptor Agonists Facilitate Retention of Avoidance Training: Participation of Dopaminergic Mechanisms," *Behav. Neural. Biol.* 59:57–62 (1993).
Brioni, Jorge., et al., "The Pharmacology of (–) Nicotine and Noval Cholinergic Channel Modulators," *Adv. Pharmacol.* 37:153–214 (1997).
Coles, Stephen J., et al., "Hypersecretion of Mucus Glycoproteins in Rat Airways Induced by Tobacco Smoke," *Am. J. Pathology,* 94:459–472 (1979).
Finnie, Ian., et al., "Stimulation of colonic mucin synthesis by corticosteroids and nicotine," *Clin. Sci.,* 91:359–364 (1996).
Forstner, G., et al., "Clinical Aspects of Gastrointestinal Mucus," *Adv. Exp. Med. Biol.* 144:199–224 (1982).

Garvey, David., et al., "Ligands for Brain Cholinergic Channel Receptors: Synthesis and in Vitro Characterization of Novel Isoxazoles and Isothiszoles as Bioisosteric Replacements for the Pyridine Ring in Nicotine," *J. Med. Chem.* 37:4455–4463 (1994).
Gipson, I., et al., "MUC4 and MUC5B Transcripts Are the Prevalent Mucin Messenger Ribonucleic Acids of the Human Endocervix," *Biology of Reproduction,* 60:58–64 (1999).
Holladay, Mark W., et al., "Natural Products as a Source of Nicotinic Acetylcholine Receptor Modulators and Leads for Drug Discovery," *Neuronal Nicotinic Receptors,* Eds. Arneric and Brioni, Wiley–Liss, Inc., 253–270(1999).
Hubbard, Gene., et al., "Evaluation of A Vaginal Moisturizer in Baboons with Decreasing Ovarian Funation," *Lab Animal Sci.* 47(1):36–39 (1997).
Hummer, B., et al., "Stimulation of Submucosal Glands by Nicotine Applied Locally to the Airway Mucosa," *Klin. Wochenschr.* 66(Suppl XI):161–169 (1988).
Kaunitz, Jonathan D., et al., "Effect of Orogastric Nicotine on Rat Gastric Mucosal Gel Thickness, Surface Cell Viability and ntracellular pH1," *J. Pharmacol. Exp. Ther.,* 265(2):948–954 (1993).
Kuo, Han–Pin., et al., "Cigarette smoke–induced airway goblet cell secretion: dose–dependent differential nerve activation," *Am. J. Physiol.* 263:L161–167 (1992).
Lang, M., et al, "Effect of Systemic Nicotine on Mucus Secretion form Tracheal Submucosal Glands and on Cardiovascular, Pulmonary, and Hematologic Variables," *Klin. Wochenschr.* 66(Suppl XI):170–179 (1988).
Latli,Bachir., et al., "Novel and Ptent 6–Choloro–3–pyridinyl Liginds for the a4B2 Neuronal Nicotinic Acetylcholine Receptor," *J. Med. Chem.* 42: 2227–2234 (1999).

(List continued on next page.)

Primary Examiner—Theodore J. Criares
Assistant Examiner—Jennifer Kim
(74) Attorney, Agent, or Firm—Albert P. Halluin; Viola T. King; Howrey Simon Arnold & White, LLP

(57) ABSTRACT

The invention provides a method for treating vaginal dryness by increasing hydration and lubrication of vaginal and cervical tissues in a subject in need of such treatment. The method comprises administering to the subject a nicotinic acetylcholine receptor agonist such as nicotine and its analogs, transmetanicotine and its analogs, epibatidine and it analogs, lobeline and its analogs, pyridol derivatives, para-alkylthiophenol derivatives, and imidacloprid and its analogs, in an amount effective to stimulate cervical and vaginal secretions. Pharmaceutical formulations and methods of making the same are also disclosed. Methods of administering the formulation include: topical administration via a liquid, gel, cream, ointment, foam, pessary, or tablet; systemic administration via nasal drops or spray, inhalation by nebulizer or other device, oral form (liquid or pill), injectable, suppository form, or transdermal form. The invention is useful for treating vaginal dryness and vulvar pain.

13 Claims, No Drawings

OTHER PUBLICATIONS

Morris, Gerald., et al., "Gastric Cytoprotection Is Secondary to Increased Mucosal Fluid Secretion: A Study of Six Cytoprotective Agents in the Rat," *J. Clin Gastroenterol,* 27(Suppl. 1):S53–63 (1998).

Pullen, Rupert D., "Colonic mucus, smoking and ulcerative colitis," *Ann. R. Coll. Surg. Engl.* 78:85–91 (1996).

Richardson, P.S., et al., "The control of airway mucus secretion," *Eur. J. Respir. Dis. Suppl.* 153:43–51 (1987).

Vernier, Jean–Michael., et al., "4–[[2–(1–Methyl–2–pyrrolidinyl)ethyl]thio]–phenol Hydrochloride SIB–1553A): A Novel Cognitive Enhancer with Selectivity for Neuronal Nicotinic Acetycholine Receptors," *J. Med. Chem.* 42: 1684–1686 (1999).

Villemagne, Victor L., et al., "Nicotine and Related Compunds as PET and SPECT Liginds," *Neuronal Nicotinic Receptors,* Eds. Arneric and Brioni, Wiley–Liss, Inc. 234–250 (1999).

Wanner, Adam., et al., "Mucociliary Clearence in the Airways," *Am. J. Respir. Crit. Care Med.,* 154:1868–1902 (1996).

Zijlstra, F.J., et al., "Effect of nicotine on rectal mucus and mucosal eicosanoids," *Gut,* 35:247–251 (1994).

* cited by examiner

METHOD FOR TREATING VAGINAL DRYNESS WITH NICOTINIC ACETYLCHOLINE RECEPTOR AGONISTS

TECHNICAL FIELD

This invention relates to a method of treating vaginal dryness by administering to a patient a nicotinic acetylcholine receptor agonist such as nicotine, epibatidine alkaloids and their analogs thereof.

BACKGROUND OF THE INVENTION

Vaginal dryness is a very common problem which brings physical and emotional distress to many women (Key, E., *Nurs. Stand.* 5:24–27 (1991)). It most commonly manifests itself during sexual intercourse, which causes dyspareunia and can eventually lead to apareunia. Although it is traditionally considered to be a condition which affects postmenopausal women, it can occur during the premenopausal and perimenopausal years. The use of oral contraceptives may also cause a reduction in vaginal moisture in some women (Reginald, W., et al., *Br. J. Obstet. Gynaecol.* 96:1148–1152 (1989)). Postpartum vaginal dryness, independent of or as a result of lactation, can be a significant complaint (Wisniewski, P., et al., *Am. J. Obstet. Gynecol.* 165:1249–1254 (1991)). Women undergoing chemotherapy or radiotherapy for malignant diseases such as leukemia often experience vaginal dryness as a result of treatment (Cust, M., et al., *Br. Med. J.* 299:1494–1497 (1989)). Many disease states, such as systemic sclerosis and other systemic autoimmune disorders (Bhadauria, S., et al., *Am. J. Obstet. Gynecol.* 172:580–587 (1995)), Ehlers-Danlos syndrome (Sorokin, Y., et al., *J. Reprod. Med.* 39:281–284 (1994)), diabetes mellitus (Sreebny, L., et al., *Diabetes Care* 15:900–904 (1992)), and Sjögren's syndrome (Marchesoni, D., et al., *Eur. J. Obstet. Gynecol. Reprod. Biol.* 63:49–53 (1995)) have decreased vaginal hydration and lubrication problems as significant disease-associated symptoms.

Vulvar pain is defined as the excessive sensitivity of the nerves supplying the mucus membrane of the vulva. This persistent burning and sensitivity in vulvar skin is not caused by identifiable infection. It cannot be cured by surgery. The diseases covered under "vulvar pain" are also referred to as vulvodynia/vulvar vestibulitis, vulvitis, burning vulvar syndrome and is often associated with fibromyalgia, irritable bowel syndrome, Sjögren's syndrome, chronic inflammation, and Paget's disease as well as in the absence of any identifiable disease or infection.

Current therapies for increasing vaginal moisture are: lubricating agents such as lubricating creams or jellies, topical estrogen creams, and HRT (hormone replacement therapy). Lubricating jellies provide short-lived and temporary relief, as these are aqueous preparations containing no pharmacologically active agent. Topical estrogen creams, if used on a regular basis, may be absorbed into the systemic circulation. This can cause endometrial stimulation and can lead to endometrial hyperplasia and carcinoma (Whitehead, M., et al., *N. Eng. J. Med.* 305:1599–1605 (1981)). HRT is effective at relieving symptoms of vaginal atrophy and hence vaginal dryness but has several contraindications and unwanted risks and side effects.

A history of gall bladder disease (*N. Eng. J. Med.*, 290:15–19 (1974)) or a personal or family history of reproductive or breast cancer (Harlap, S., *Am. J. Obstet. Gynecol.* 166:1986–1992 (1992)) are contraindications for estrogen therapy. Other contraindications are: history of stroke, cardiovascular disease, deep-vein thrombosis, superficial thrombophlebitis, liver disease, heavy smoking, high blood pressure, diabetes, uterine bleeding or large fibroids, hyperlipidemia, and gross obesity (Lichtman, R., *J. Nurse Midwifery* 36:30–48 (1991)). One major disadvantage of HRT is the resumption of monthly withdrawal bleeds, which many postmenopausal women will not accept. Some women, even while on HRT, still experience a degree of vaginal dryness (Key, E., *Nurs. Stand.* 5:24–27 (1991)).

Mucus is a viscous, lubricating material that recruits and maintains moisture to the surfaces it coats. Mucus is actively secreted with salt and water onto surfaces that require these hydrating and lubricating properties for normal functioning (Forstner et al., *Adv. Exp. Med. Biol.* 144:199–224 (1982)). The mucus covering on the surfaces of the female reproductive tract is important in its defense and reproductive function. The mucus gel, secreted primarily by the endocervical epithelium, provides a barrier to sperm and pathogen penetrance into the endometrium and a protective covering for the vaginal epithelium. The hydration of vaginal and cervical mucus prevents atrophy, provides lubrication during intercourse, aids surface defense against pathogens, and modulates sperm entry into the uterus, etc. (see Gipson I. K., et al., *Biology of Reproduction*, 60, 58–64 (1999))

Nicotinic acetylcholine receptors (nAChRs), present in a variety of tissues, are heterologous receptors made up of several subunits. Various nAChR subtypes exist and they show a complex regulation of calcium concentration and mediation of neurotransmitter (e.g. dopamine) release.

Nicotinic agonists have many pharmacological actions when applied locally or systemically, and synthetic compounds are being targeted towards a number of therapeutic indications including: Alzheimer's disease, Parkinson's disease, smoking cessation, epilepsy, neuroprotection, attention deficit disorder and pain (*Neuronal Nicotinic Receptors: Pharmacology and Therapeutic Opportunities*, Eds. Arneric and Brioni, Wiley-Liss, Inc. (1999)). Nicotinic agonists, such as nicotine, stimulate the secretion of mucus when applied to the mucosal surfaces of the lung and stomach, and is believed to have protective effects on ulcerative colitis presumably by increasing colonic mucin secretion (Morris, et al., *J. Clin Gastroenterol*, 27:S53–63 (1998), Finnie, et al., *Clin. Sci.*, 91:359–364 (1996), Zijlstra, et al., *Gut*, 35:247–251 (1994); Kaunitz, et al., *J. Pharmacol. Exp. Ther.*, 265:948–954 (1993)). Transdermnal nicotine has been used clinically as therapy for ulcerative colitis (Pullen, *Ann. R. Coll. Surg. Engl.* 78:85–91 (1996)).

The nicotine-associated effects of cigarette smoking have been studied extensively and it is well established that tobacco smoking leads to chronic bronchitis and mucus hypersecretion (Coles, et al., *Am. J. Pathology*, 94:459–471 (1979); Wanner, et al., *Am. J. Respir. Crit. Care Med.*, 154:1868–1902, (1996). "Topical" tobacco smoke causes mucin secretion from airway goblet cells and systemic nicotine causes increased tracheal mucus secretion (Kuo, et al., *Am. J. Physiol.* 263:L161–167 (1992); Lang, et al.; *Klin. Wochenschr.* 66:170–179 (1988); Hummer, et al., *Klin. Wochenschr.* 66:161–169 (1988), Richardson, et al., *Eur. J. Respir. Dis. Suppl.* 153:43–51 (1987)). These pro-secretory effects of nicotine have been largely thought of as deleterious, with the exception of the association of less frequent ulcerative colitis among cigarette smokers.

Recent advances in the field of nicotine receptors has revealed that it is possible to create ligands for specific nicotinic receptor subtypes, thereby reducing or eliminating altogether the unwanted side effects of nicotine, such as neuromotor and cardiovascular effects (Brioni et al., *Behav.*

*Neural. Biol.* 59:57–62 (1993); Brioni, et al., *Adv. Pharmacol.* 37:153–214 (1997)) The field of therapeutic nicotinic agonists largely focuses on the central nervous system effects of nicotinic agonists and their ability to stimulate cognition (U.S. Pat. Nos. 5,922,723 and 5,861,423). The mild antiinflammatory effects of nicotine are established; smokers have been shown to have a lower incidence of inflammatory diseases such as ulcerative colitis, sarcoidosis, pigeon breeder's disease, farmer's lung, allergies, endometriosis, uterine fibroids and acne (Arneric & Brioni Ch. 11, p. 205). Nicotine has also been investigated for its effects on CNS inflammation (Brioni, et al., (1997), supra) based diseases.

Because of the ability of nicotinic agonists to stimulate secretion in the lung and gastrointestinal tract, Applicants were motivated to investigate whether nicotinic agonists could effect hydration and lubrication of the vaginal and cervical tissues, and thus be effective in treating vaginal dryness. Applicants have discovered that nicotinic receptor agonists, when given topically or systemically, provide a therapeutic effect of treating vaginal dryness by increasing the hydration and lubricating properties of vaginal and cervical tissues.

SUMMARY OF THE INVENTION

The invention provides a method of stimulating cervical and vaginal secretion in a subject in need. The method comprises administering to a patient a pharmaceutical composition comprising a nicotinic acetylcholine receptor agonist in an amount effective to increase cervical and vaginal hydration.

The pharmaceutical composition used in this invention comprises a nicotinic receptor agonist together with a pharmaceutically acceptable carrier thereof. Nicotinic receptor agonists include but are not limited to: nicotine and its analogs, trans-metanicotine and its analogs, epibatidine and its analogs, pyridol derivatives, piperidine alkaloids such as lobeline and its analogs, certain para-alkylthiophenol derivatives, and imidacloprid and its analogs.

The compounds of the present invention are potent agonists of nicotinic receptors; thus, they are useful in the treatment of vaginal dryness in which hydration and lubrication of vaginal and cervical tissues are impaired.

DETAILED DESCRIPTION OF THE INVENTION

The invention provides methods for treating vaginal dryness using a nictonic receptor agonist. The method comprises topically or systemically administering to a subject in need thereof a pharmaceutical composition comprising a nicotinic receptor agonist in an amount effective to stimulate mucin secreting epithelial cells to secrete mucin, thereby increasing hydration and lubrication in vaginal and cervical tissues. The nicotinic receptor agonist stimulates nicotinic acetylcholine receptors, which leads to prosecretory effects, either directly via neural stimulation or indirectly through stimulation of dopamine release. The methods of the present invention may be used exclusive of, or as an adjunct to, hormone replacement therapy (HRT) or estrogen replacement therapy (ERT). The present invention provides a method of treating a mammal with vaginal dryness arising from, but not limited to, menopause, childbirth, breastfeeding, chemotherapy or radiotherapy, diabetes mellitus, Sjögren's syndrome, Ehlers-Danlos syndrome, systemic sclerosis and other systemic autoimmune diseases, hysterectomy, urogenital surgery, psychosomatic disorders, anxiety, psychosexual problems, and pharmacological drug-related side effects.

It is also contemplated that the method of the present invention can be used to increase vaginal moisture and lubrication in healthy women for the purpose of facilitating sexual intercourse. It is further contemplated that the method of the present invention would be particularly useful for a woman who wished to accommodate a sexual partner who is undergoing treatment with Viagra® or other such drugs used for the treatment of erectile dysfunction.

The pharmaceutical compositions useful in this invention comprise a nicotinic acetylcholine receptor agonist (Formulae I–X) together with a pharmaceutically acceptable carrier therefor. Useful compositions also include a nicotinic receptor agonist bound to a polymer such as polyethyleneglycol; such compositions are not absorbed systemically.

Various nicotine cholinergic receptor agonists are described in Benowitz, et al., P 213–234; Villemagne, et al., p. 235–250; and Holladay, et al., P. 253–270 in *Neuronal Nicotinic Receptors*, Eds. Arneric and Brioni, Wiley-Liss, Inc. (1999); Vernier, et al., *J. Med. Chem.* 42: 1684–1686 (1999), and Latli, et al., *J. Med. Chem.* 42: 2227–2234 (1999). Nicotinic receptor agonists include but are not limited to: nicotine and its analogs, trans-metanicotine and its analogs, epibatidine and its analogs, pyridol derivatives, piperidine alkaloids such as lobeline and its analogs, and certain para-alkylthiophenols.

Nicotine and its analogs are depicted by general formula I:

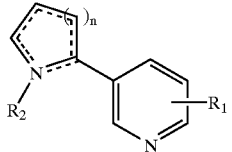

Formula I

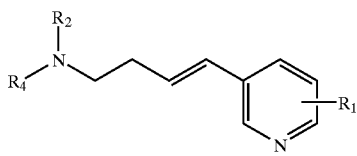

Formula II

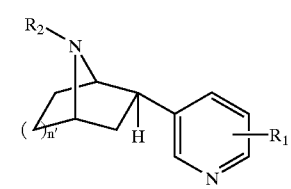

Formula III

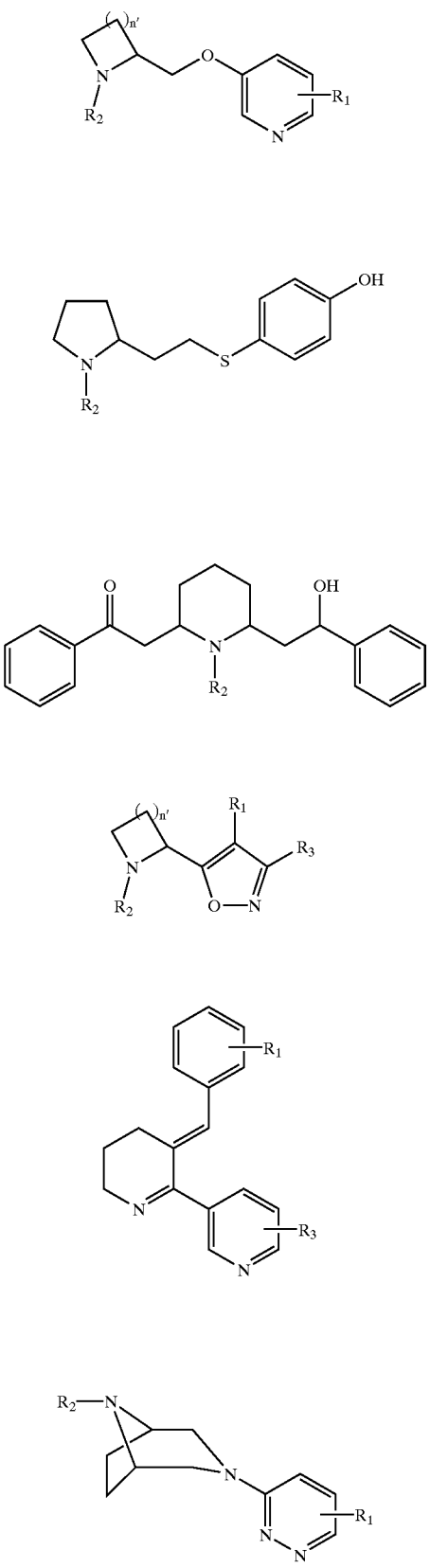

Formula IV

Formula V

Formula VI

Formula VII

Formula VIII

Formula IX

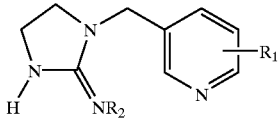

Formula X wherein:

n is an integer between 0–3;

n' is an integer between 1–3;

$R_1$ and $R_3$ are H, $C_1$–$C_6$ alkyl, $C_2$–$C_6$ alkenyl, $C_2$–$C_6$ alkynyl, $C_3$–$C_7$ cycloalkyl, $C_4$–$C_7$ cycloalkenyl, $C_1$–$C_6$ alkoxy, F, Cl, Br, I, or amino; wherein at least one hydrogen of aid alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{1-4}$ alkylamino, and di-$C_{1-4}$ alkylamino, wherein said alkyl groups are optionally linked to form a heterocycle; and $R_2$ and $R_4$ are H, $C_1$–$C_6$ alkyl, $C_2$–$C_6$ alkenyl, $C_2$–$C_6$ alkynyl, $C_3$–$C_7$ cycloalkyl, $C_4$–$C_7$ cycloalkenyl, $C_1$–$C_6$ alkoxy, or amino; wherein at least one hydrogen of said alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{1-4}$ alkylamino, and di-$C_{1-4}$ alkylamino, wherein said alkyl groups are optionally linked to form a heterocycle; optionally $R_2$ and $R_4$ in Formula II are linked to form a 5 or 6-membered ring.

The stereochemistry of compounds of Formulae I to X useful in this invention can be either levoratatory (S)-isomer, (R)-isomer, or a mixture of R/S isomers (racemic).

Nicotine analogs of Formula I useful in this invention include nicotine, 5-ethynylnicotine, nomicotine, cotinine, nicotyrine, nicotine-N'-oxide, anabasine, anatabine, myosmine, β-nornicotyrine, N'-methylanabasine, N'-methylanatabine, N'-methylmyosmine, and 2, 3'-bipyridyl. Preferred compounds, for example, are: (–)-nicotine, anabasine, and 5-ethynylnicotine.

Preferred compounds of Formula II include trans-metanicotine and 3-ethoxy-trans-metanicotine (without N-methyl group).

Preferred epibatidine analogs of Formula III include epibatidine and its derivatives wherein the chlorine (Cl) on the pyridine ring is replaced by F, Br, I, H, or methyl.

Preferred compounds of Formula IV include [2-methyl-3-(2-(S)-pyrrolidinylmethoxy) pyridine dihydrochloride], ABT-089 (n=2, $R_1$=1-methyl and $R_2$=H); -(2-azetidinyl-methoxy)-2-chloropyridine, ABT-594 (n=1, $R_1$=2-chloro and $R_2$=H).

Preferred compounds of Formula V include thioalkylphenol derivatives with $R_1$=methyl, trifluoromethyl, or ethyl. An example of a preferred compound is 4-[[2-(1-methyl-2-pyrrolidinyl)ethyl]thio]phenol hydrochloride (SIB-1553A)

Preferred compounds of Formula VI are lobeline analogs with $R_1$=$CH_3$ (lobeline) or $R_1$=ethyl.

Preferred compounds of Formula VII include (S)-3-methyl-5-(1-methyl-2-pyrrolidinyl) isoxazole hydrochloride, ABT-418 (n=2, $R_1$=3-methyl and $R_2$=$CH_3$); and n=2, $R_1$=ethynyl, $R_2$=$CH_3$.

Preferred compounds of Formula VIII include $R_1$=2,4-dimethoxy (known as DMXB); $R_1$=2,4-diethoxy; or $R_1$=2, 4-dichloro.

Preferred compounds of Formula IX include $R_1$=6-chloro and $R_2$=H (DBO-083); and $R_1$=6-chloro and $R_2$ =methyl.

Preferred compounds of Formula X include imidacloprid ($R_{1=Cl,\ R2}$=NO$_2$), desnitro-imidacloprid ($R_1$=Cl, $R_2$=H).

Some compounds of Formulas I–X can be made by methods known to those skilled in the art; some compounds are commercially available, for example from Sigma Chemical Co. (St. Louis, Mo.). Compounds of Formula I and VIII can be made in accordance with known procedures described by Kem et al. (U.S. Pat. No. 5,741,802) and McDonald et al. (U.S. Pat. No. 5,723,477). Compounds of Formula II can be made in accordance with known procedures described by Caldwell et al. (U.S. Pat. No. 5,861,423). Compounds of Formula III can be made in accordance with known procedures described by Bencherif et al. (U.S. Pat. No. 5,922,723), Shen et al. (U.S. Pat. No. 5,817,679), and Badio et al. (*Eur. J. Pharmacol.* 321:189–194 (1997)).

Compounds of Formula IV can be made in accordance with known procedures described by Nan-Horng et al. (WO/9746554A1). Compounds of Formula V can be made in accordance with known procedures described by Vernier et aL, *J. Med. Chem.* 42:1684–6 (1999). Compounds of Formula VI can be made in accordance with known procedures described by Crooks et al (U.S. Pat. No. 5,830,904). Compounds of Formula VII can be made in accordance with known procedures described by Garvey, et al. *J. Med. Chem.* 37:4455–63 (1994). Formula X can be made in accordance with known procedures described by Latli et al., *J. Med. Chem.* 42:2227–34 (1999).

The active compounds of the invention may also be present in the form of their pharmaceutically acceptable salts, such as, but not limited to, an acid salt such as acetates, tartrates, chloride, phosphate, sulfates, sulfites, carbonates, bicarbonate and citrates. Pharmaceutically acceptable salts are salts that retain the desired biological activity of the parent compound and do not impart undesired toxicological effects.

The compounds disclosed herein may be administered to the cervical and/or vaginal mucosa of a patient by any suitable means, but are preferably administered by a solution, gel, suspension, cream, ointment, foam, pessary, or tablet containing the active compound. Alternatively, the active compounds may by administered by continuous release from a vaginal ring (Stumpf, P., *Obstet. Gynecol.* 75:9S (1990)) or an intrauterine device (Andersson, K., et al., *Obstet. Gynecol.* 79:963 (1992)).

The topical solution, gel, jelly, ointment, cream, foam, pessary, or tablet contain the active compound in a physiologically compatible vehicle, as those skilled in the art of gynecological topical delivery system development can select using conventional criteria.

Solutions formulated for administration to the vagina are usually referred to as irrigations. These are sterile solutions, prepared in a manner typical of sterile injections that are intended for prepared as a single use sterile solution.

Gels or jellies may be produced using a suitable gelling agent including, but not limited to, gelatin, tragacanth, or a cellulose derivative and may include glycerol as a humectant, emollient, and preservative.

Ointments are semi-solid preparations that consist of the active ingredient incorporated into a fatty, waxy, or synthetic base.

Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Pessaries are solid unit-dose forms suitably shaped for insertion into the vagina and may either be composed of a base that melts at body temperature or which dissolves when in contact with mucous secretions. Examples of suitable bases include, but are not limited to, theobroma oil, synthetic fat bases (e.g. Witepsol), polyethylene glycols (macrogols), and glycerol suppository basis.

Vaginal tablets are composed of the active ingredient contained within a solid dosage form base which may include, but not be limited to, excipients such as lactose, microcrystalline cellulose, corn starch, magnesium stearate, silicon dioxide, and hydroxypropyl methylcellulose.

In addition to the topical administration described above, there are various methods of administering the active compounds systemically. One such means involve an aerosol suspension of respirable particles comprised of the active compound, which the subject inhales. The active compound is absorbed into the bloodstream via the lungs and contact the cervical and/or vaginal tissues in a pharmaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another means of systemically administering the active compounds to the cervical and vaginal tissues of the subject involve administering a liquid/liquid suspension in the form of nasal drops of a liquid formulation, or a nasal spray of respirable particles which the subject inhales. Liquid pharmaceutical compositions of the active compound for producing a nasal spray or nasal drops are prepared by combining the active compound with a suitable vehicle, such as sterile pyrogen free water or sterile saline by techniques known to those skilled in the art.

Other means of systemic administration of the active compound involve oral administration, in which pharmaceutical compositions containing compounds of Formulae I–X are in the form of tablets, lozenges, aqueous or oily suspensions, dispersible powders or granules, emulsion, hard or soft capsules, or syrups or elixirs. Compositions intended for oral use may be prepared according to any method known to the art; such compositions may contain one or more agents selected from the group consisting of sweetening agents, flavoring agents, coloring agents, and preserving agents in order to provide pharmaceutically elegant and palatable preparations. Tablets may be prepared to contain the active ingredient in admixture with nontoxic pharmaceutically acceptable excipients which are suitable for the manufacture of tablets. These excipients may be, for example, inert diluents, such as calcium carbonate, sodium carbonate, lactose, calcium phosphate, or sodium phosphate; granulating and disintegrating agents, for example, corn starch or alginic acid; binding agents, for example, starch, gelatin, or acacia; and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example, peanut oil, liquid paraffin, or olive oil.

The active compounds may also be delivered to the cervical and vaginal tissues of a subject through absorption by the skin using transdermal patches or pads. Suitable transdermal systems include: Nicoderm, with a drug reservoir and a rate-controlling membrane; Nicotinell, with a nicotine solution dispersed in a cotton gauze pad between layers of adhesive; and Niconil, with a nicotine gel matrix. (Matsushima et al., *J. Pharm. Sci.*, 84:365–369 (1995)). The active compounds are absorbed into the bloodstream through the skin. Plasma concentration of the active compounds can be controlled by using patches containing different concentrations of active compounds.

Additional means of systemic administration of the active compound to the cervical and vaginal tissues of the subject involve a suppository form of the active compound, such that a therapeutically effective amount of the compound reaches the cervical and vaginal tissues via systemic absorption and circulation.

For systemic administration, plasma concentrations of active compounds delivered by any means may vary according to compounds, but are generally 0.1–100 ng/ml; preferably, 0.5–50 ng/ml; and more preferably, 5–25 ng/ml.

For topical administration, the daily dose may vary depending on the solubility of a particular formulation of the active compound administered. The daily dose may be divided among one or several unit dose administrations. For example, a regimen may be administered up to four times per day or on an as needed basis to address acute exacerbation. The total topical daily dose of a nicotonic acetylcholine receptor agonist may range from 0.001–200 mg; preferably, 0.01–100 mg; and more preferably, 0.1–10 mg; depending upon the age and state of the subject.

The invention is illustrated further by the following examples of treatment which are not to be construed as limiting the scope or spirit to the specific procedures described in them.

EXAMPLES

Example 1. In vivo study in rabbits

The compounds of the invention are evaluated in vivo by topically administrating a compound of Formulae I–X to the cervical or vaginal tissue of an animal in a therapeutic effective amount to stimulate mucin secretion. Specifically, 0.001–200 mg of a compound of Formulae I–X is topically applied to the cervical or vaginal tissue of an ovariectomized female white albino New Zealand rabbit. Then the treated animal is subjected to a gynecological examination and graded by a qualified medical specialist on a scale of 1 to 5 of a vaginal atrophy index, including a measurement of fluid pH. (Hubbard, G. et al., *Lab Animal Sci.* 47, 36–39, (1997)).

A vaginal smear of the treated rabbit is then obtained with a cotton swab. The sample is appropriately prepared; the relative amount of representative cervical mucins is determined and compared with that of a non-treated control rabbit by an ELISA or a calorimetric dot blot method (Gipson, I. et al., *Biol. Reprod.*, 56:999–1011 (1997)).

Example 2. Stimulation of Mucin Release from Mucosal Goblet Cells

The following is an example of a method for measuring the effects of a nicotinic receptor agonist in vivo on mucin secretion from mucous membranes using impression cytology. Impression cytology is a technique used to stain and identify mucin-containing goblet cells (Rolando, M., et al., *Adv. Exp. Med. Bio.*, 350:249 (1994)).

A compound of Formulae I–X or a saline solution is applied to the mucosal surface and impression cytology is performed at 5, 15, 30 and 60 minutes after application of solution. The specimens are stained with periodic acid and Schiff's reagent (AB-PAS), and the area of PAS staining is analyzed by computer software (Winroof or BioQuant). A decrease in the area of AB-PAS staining compared to saline control indicates that the compound stimulates mucin secretion from goblet cells of mucus membranes.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of stimulating cervical and vaginal secretions comprising administering to a subject in need of such treatment a therapeutically effective amount of a nicotinic acetylcholine receptor agonist in a pharmaceutically effective carrier, wherein said nicotinic acetylcholine receptor agonist is a compound of Formula II:

Formula II

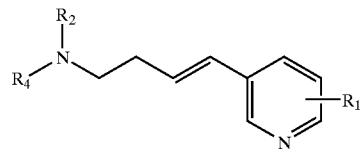

wherein:

$R_1$ is H, $C_1$–$C_6$ alkyl, $C_2$–$C_6$ alkenyl, $C_2$–$C_6$ alkynyl, $C_3$–$C_7$ cycloalkyl, $C_4$–$C_7$ cycloalkenyl, $C_1$–$C_6$ alkoxy, F, Cl, Br, I, or amino; wherein at least one hydrogen of said alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{1-4}$ alkylamino, and di-$C_{1-4}$ alkylamino; and $R_2$ and $R_4$ are independently H, $C_1$–$C_6$ alkyl, $C_2$–$C_6$ alkenyl, $C_2$–$C_6$ alkynyl, $C_3$–$C_7$ cycloalkyl, $C_4$–$C_7$ cycloalkenyl, $C_1$–$C_6$ alkoxy, or amino; wherein at least one hydrogen of said alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{1-4}$ alkylamino, and di-$C_{1-4}$ alkylamino; optionally $R_2$ and $R_4$ in Formula II are linked to form a 5 or 6-membered ring.

2. The method according to claim 1, wherein said nicotinic acetylcholine receptor agonist is trans-metanicotine and its analogs.

3. The method according to claim 1, wherein said administering involves topical administration of said compound.

4. The method according to claim 3, wherein said compound is administered in a form of a solution, a gel, a suspension, a cream, an ointment, a foam, a pessary or a tablet.

5. The method according to claim 1, wherein said administering is systemic administration of said compound.

6. The method according to claim 5, wherein said compound is systemically administered by an aerosol suspension of respirable particles containing said compound.

7. The method according to claim 5, wherein said systemic administration involves administration of a liquid/liquid suspension of said compound via nose drops or nasal spray, or administration of a nebulized liquid to oral or nasopharyngeal airways of said subject, such that a therapeutically effective amount of said compound contacts vaginal or cervical tissues of said subject via systemic absorption and circulation.

8. The method according to claim 5, wherein said systemic administration of said compound is accomplished by administering an oral form of said compound, such that a therapeutically effective amount of said compound contacts vaginal or cervical tissues of said subject via systemic absorption and circulation.

9. The method according to claim 8, wherein said oral form is a chewable gum.

10. The method according to claim 5, wherein said systemic administration is administration of an injectable form of said compound, such that a therapeutically effective amount of said compound contacts vaginal or cervical tissues of said subject via systemic absorption and circulation.

11. The method according to claim 5, wherein said systemic administration involves administration of a suppository form of said compound, such that a therapeutically effective amount of said compound contacts vaginal or cervical tissues of said subject via systemic absorption and circulation.

12. The method according to claim 5, wherein said systemic administration involves administration of said compound in a form of a transdermal patch or a transdermal pad, such that a therapeutically effective amount of said compound contacts vaginal or cervical tissues of said subject via systemic absorption and circulation.

13. A method of increasing vaginal lubrication in a mammal comprising the steps of administering to a subject an amount of a nicotinic acetylcholine receptor agonist effective to stimulate cervical and vaginal secretion, wherein said nicotinic acetylcholine receptor agonist is a compound of Formula II:

Formula II

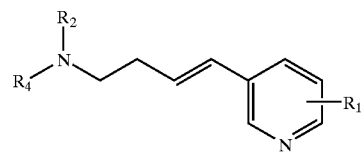

wherein $R_1$ is H, $C_1$–$C_6$ alkyl, $C_2$–$C_6$ alkenyl, $C_2$–$C_6$ alkynyl, $C_3$–$C_7$ cycloalkyl, $C_4$–$C_7$ cycloalkenyl, $C_1$–$C_6$ alkoxy, F, Cl, Br, I, or amino; wherein at least one hydrogen of said alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{4-1}$ alkylamino, and di-$C_{1-4}$ alkylamino; and $R_2$ and $R_4$ are independently H, $C_1$–$C_6$ alkyl, $C_2$–$C_6$ alkenyl, $C_2$–$C_6$ alkynyl, $C_3$–$C_7$ cycloalkyl, $C_4$–$C_7$ cycloalkenyl, $C_1$–$C_6$ alkoxy, or amino; wherein at least one hydrogen of said alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{1-4}$ alkylamino, and di-$C_{1-4}$ alkylamino; optionally $R_2$ and $R_4$ in Formula II are linked to form a 5 or 6-membered ring.

* * * * *